United States Patent [19]

Bellut

[11] Patent Number: 4,970,347

[45] Date of Patent: Nov. 13, 1990

[54] METHOD OF PRODUCING 2, 6, 6-TRIMENTHYL-2-CYCLOHEXENE-1, 4-DIONE

[75] Inventor: Hans Bellut, Bergstrasse, Fed. Rep. of Germany

[73] Assignee: Huels Aktiengesellschaft, Marl, Fed. Rep. of Germany

[21] Appl. No.: 434,283

[22] Filed: Nov. 13, 1989

[30] Foreign Application Priority Data

Dec. 17, 1988 [DE] Fed. Rep. of Germany ....... 3842547

[51] Int. Cl.$^5$ ............................................ C07C 45/34
[52] U.S. Cl. ................................................... 568/344
[58] Field of Search ......................................... 568/344

[56] References Cited

U.S. PATENT DOCUMENTS

| | | |
|---|---|---|
| 3,944,620 | 3/1976 | Becker et al. ................... 568/344 |
| 3,960,966 | 6/1976 | Widmar et al. .................. 568/344 |
| 4,026,947 | 5/1977 | Costantini et al. ............... 568/344 |
| 4,026,948 | 5/1977 | Becker et al. ................... 568/344 |
| 4,046,813 | 9/1977 | Brenner ........................... 568/344 |
| 4,092,361 | 5/1978 | Costantini et al. ............... 568/344 |
| 4,157,352 | 6/1979 | Brenner ........................... 568/344 |

FOREIGN PATENT DOCUMENTS

| | | |
|---|---|---|
| 2457157 | 6/1975 | Fed. Rep. of Germany ...... 568/344 |
| 63-122644 | 5/1988 | Japan ............................... 568/344 |

*Primary Examiner*—James H. Reamer
*Attorney, Agent, or Firm*—Oblon, Spivak, McClelland, Maier & Neustadt

[57] ABSTRACT

A method of producing 2,6,6-trimethyl-2-cyclohexene-1,4-dione. Cu(II)acetylacetonate is used as a catalyst, with a suitable amount of pyridine, in the absence of solvents. The product may be used as an intermediate product for producing flavors and fragrances, or for producing vitamin E and vitamin A.

9 Claims, No Drawings

METHOD OF PRODUCING 2, 6, 6-TRIMENTHYL-2-CYCLOHEXENE-1, 4-DIONE

BACKGROUND OF THE INVENTION

1. Field of the Invention:

This invention is directed to a method of producing 2,6,6-trimethyl-2-cyclohexene-1,4-dione.

2. Discussion of the Background:

2,6,6-Trimethyl-2-cyclohexene-1,4-dione (ketoisophorone, KIP) is a valuable starting substance for syntheses in terpene chemistry. It can also be employed as a convenient and inexpensive basis for producing vitamin compounds of the A series and vitamin E, and also for producing flavors and fragrances which are identical to natural products (see, for example, Isler, O. 1971, "Carotenoids", pub. Birkhaeuser Verlag, Basel and Stuttgart).

KIP is advantageously synthesized by the catalytic oxidation with oxygen of 2,6,6-trimethyl-2-cyclohexene1-one (alpha-isophorone, alpha-IP) or, preferably, of 3,5,5-trimethyl-3-cyclohexene-1-one (beta-isophorone, beta-IP) (see, Ger. OS 25 26 851, Neth. OS 74 15 848, and Ger. OS 24 57 157 and OS 25 15 304). A problem when using alpha-isophorone is the large number of byproducts which make refinement of the product mixture difficult. For a long time there was no known satisfactory means of producing beta-isophorone. Furthermore, the method is excessively costly if good results are desired in terms of the amount and quality of the KIP product.

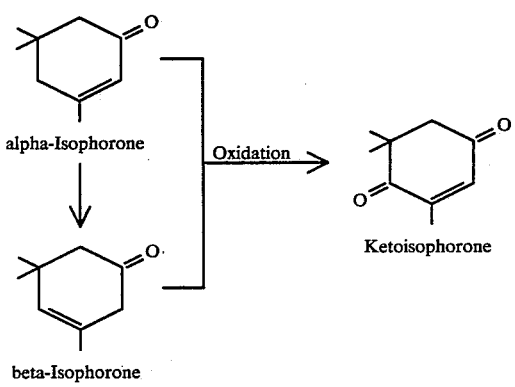

Recently the problem of producing beta-isophorone was solved by a new method of isomerizing alphaisophorone (Ger. OS 37 35 211). Therefore the starting product is now available in sufficient quantity and at a satisfactory price.

Beta-isophorone is oxidized to KIP according to Ger. OS 25 15 304 by oxygen or an oxygen-containing gas, with the aid of a lead, vanadium, chromium, manganese, iron, or cobalt salt, optionally in the presence of an organic nitrogen base, e.g. pyridine.

The usual transition metals are less suitable for the reaction, however, because they are particularly good catalysts for the equilibrium reaction between beta-isophorone and alpha-isophorone, and thus their use leads to appreciable back-isomerization (Ger. OS 37 35 211).

In the case of Ger. OS 25 15 304, a large excess of nitrogen base is employed (molar ratio of betaisophorone : pyridine =130 :330), with the aim of increasing yield and suppressing by-products. It is also recommended that a second solvent be added. The eventual removal of the large amount of nitrogen base (by distillation) is attended by high costs.

It is known according to Ger. OS 24 57 157 to use Cu(II) acetylacetonate as a catalyst in the air oxidation of beta-isophorone to KIP; however, the yield is only about 50%.

A need continues to exist for a method of producing KIP from beta-isophorone, with the use of suitable catalysts, which method provides good yields, does not require an additional solvent, and, if possible, enables operation with a reduced amount of nitrogen base.

SUMMARY OF THE INVENTION

Accordingly, one object of the present invention is to provide a method for producing KIP which avoids the problems associated with prior art methods.

This and other objects which will become apparent from the following specification have been achieved by the present method of producing 2,6,6-trimethyl-2-cyclohexene-1,4-dione by catalytic oxidation of betaisophorone with oxygen using oxygen-containing gases, with the use of a metal catalyst and a nitrogen base, where Cu(II) acetylacetonate is used as a catalyst, with addition of pyridine, in the absence of additional solvents.

DETAILED DESCRIPTION OF THE PREFERRED EMBODIMENTS

Surprisingly, only a limited amount of nitrogen base is required in the present method, as a result of the use of the Cu catalyst. In comparison to the known methods, which expressly require the concentration of the feedstock to be kept low in order to achieve high yields, in the present method, the concentration of the feedstock is increased by a factor of about 10. This accordingly brings a reduction in the cost of removing the base. This reduction in base is achieved at no reduction in yield. Moreover, not only is it unnecessary to add additional solvents, but such addition (e.g. of isopropanol) may actually be harmful.

It is preferred to operate at a molar ratio of beta-isophorone : pyridine : Cu complex of about 100-150:-20-50:0.2-5, preferably 125-135:25-40:0.5-1.5, particularly preferably about 130:30:1.

The practical details of the method can take varying forms. Excess oxygen, air or other gas (nitrogen) containing oxygen may be passed through the reaction mixture under vigorous agitation at about 20-100° C., particularly at about 50-80° C. The amount of catalyst is generally 0.1-5 wt. % Cu complex, particularly 0.5-1.5 wt. % (based on the weight of the beta-isophorone employed). In another embodiment, the reaction mixture is pumped in a recycle loop through a heatable column of appropriate dimensions, packed with glass helices, and oxygen or air is passed countercurrently through the apparatus.

The progress of the reaction can be followed by gas chromatography (GC), until the beta-isophorone is practically completely consumed. Conversions of the beta-isophorone of up to 97% can be achieved in this manner. The products comprise alpha-isophorone (about 1.5%), KIP (about 85-90%), and higher condensates not further characterized (about 10%). The alphaisophorone and residual beta-isophorone can be reprocessed for recycle-feedstocks. Accordingly, yields of 90% or more are possible.

Other features of this invention will become apparent in the course of the following descriptions of exemplary embodiments which are given for illustration of the invention and are not intended to be limiting thereof.

EXAMPLES

Example 1:

In a gas-liquid contacting apparatus, 176 g 93% beta-isophorone, 22 g pyridine, and 1.76 g Cu(II) acetylacetonate were heated to 60° C. with vigorous stirring (1,500 rpm). Then, oxygen was introduced at 39 liter/hr, for 8 hr. After the reaction began, the internal temperature first rose to about 75° C., later decreasing slowly to the bath temperature. The progress of the reaction was followed by hourly sampling and GC analysis.

TABLE 1

| Time, (hr) | Beta-IP (% by GC) | Alpha-IP (% by GC) | KIP (% by GC) | Higher Condensates (% by GC) | Yield of KIP (% by GC) |
|---|---|---|---|---|---|
| 0 | 93 | 5 | — | — | — |
| 1 | 69 | 4 | 24 | 3 | 26 |
| 2 | 41 | 3 | 48 | 7 | 52 |
| 3 | 24 | 3 | 63 | 9 | 69 |
| 4 | 11 | 3 | 76 | 10 | 81 |
| 5 | 6 | 3 | 81 | 10 | 87 |
| 6 | 3 | 3 | 83 | 11 | 89 |
| 7 | 2 | 3 | 84 | 11 | 90 |
| 8 | 1 | 3 | 84 | 11 | 90 |

The first step in product refinement is predistallation under a vacuum, in order to separate all volatiles from the residue (13.4 g) comprised of higher condensates and catalyst. This was followed by fractionation:

Fraction I: Boiling point = 65°–69° C.; 18.6 g containing KIP (74%) and alpha- and beta-isophorone (26%).

Fraction II: Boiling point = 69°–73° C.; 134.1 g containing KIP in the amount of 98%.

Fraction III: Residue = 1.5 g.

The pyridine used was captured in a cold trap in the pre-distillation and the fractionation.

Examples 2 to 5 (Comparison Examples):

Similarly to Example 1, test reactions using various other catalysts were carried out. In all cases the reaction mixture was studied by GC following the termination of the conversion. The results are summarized in Table 2.

TABLE 2

| Example No. | Catalyst* | Reaction time (hr) | beta-IP | alpha-IP | KIP | Higher condensates |
|---|---|---|---|---|---|---|
| 2 | Fe-Acetylacetonate | 8 | 24.2 | 6.7 | 51.3 | 17.7 |
| 3 | VOSO$_4$ | 15 | 8.2 | 15.9 | 59.5 | 16.1 |
| 4 | VO-Acetylacetonate | 15 | 5.8 | 8.6 | 73.8 | 12.0 |
| 5 | Cu-Acetylacetonate | 15 | 10.9 | 4.4 | 60.5 | 24.2 |

*The catalyst was dissolved in 22 g isopropanol

Obviously, numerous modifications and variations of the present invention are possible in light of the above teachings. It is therefore to be understood that within the scope of the appended claims, the invention may be practiced otherwise than as specifically described herein.

What is new and desired to be secured by Letters Patent of the United States is:

1. A method of producing 2,6,6-trimethyl-2-cyclohexene-1,4-dione, comprising:
   catalytically oxidizing beta-isophorone by contacting beta-isophorone with oxygen or an oxygen-containing gas in the presence of Cu(II)acetylacetonate catalyst and pyridine in the absence of additional solvent.

2. The method according to claim 1, wherein the molar ratio of beta-isophorone : pyridine : catalyst is 100–150:20–50:0.2–5.

3. The method according to claim 1, wherein the molar ratio of beta-isophorone:pyridine:catalyst is 125–135 : 25–40 : 0.5–1.5.

4. The method according to claim 1, wherein the molar ratio of beta-isophorone:pyridine:catalyst is about 130:30:1.

5. The method according to claim 1, wherein the amount of said catalyst is 0.1–5 wt % based on the weight of the beta-isophorone.

6. The method according to claim 5, wherein the amount of said catalyst is 0.5–1.5 wt %.

7. The method according to claim 1, wherein said oxidizing step is conducted at a temperature of about 20°–100° C.

8. The method according to claim 7, wherein said oxidizing step is conducted at a temperature of about 50°–80° C.

9. The method according to claim 1, wherein said oxidizing step is conducted by passing said oxygen or oxygen-containing gas through a mixture of said betaisophorone, catalyst and pyridine in a countercurrent manner.

* * * * *